(12) United States Patent
Tass

(10) Patent No.: US 11,141,555 B2
(45) Date of Patent: Oct. 12, 2021

(54) APPARATUS AND METHOD FOR CALIBRATING ACOUSTIC DESYNCHRONIZING NEUROSTIMULATION

(71) Applicant: GRETAP AG, Zug (CH)

(72) Inventor: Peter Alexander Tass, Tegernsee (DE)

(73) Assignee: GRETAP AG, Zug (CH)

( * ) Notice: Subject to any disclaimer, the term of this patent is extended or adjusted under 35 U.S.C. 154(b) by 114 days.

(21) Appl. No.: 16/448,472

(22) Filed: Jun. 21, 2019

(65) Prior Publication Data
US 2020/0046934 A1 Feb. 13, 2020

Related U.S. Application Data

(62) Division of application No. 14/910,412, filed as application No. PCT/EP2014/066611 on Aug. 1, 2014, now Pat. No. 10,328,233.

(30) Foreign Application Priority Data

Aug. 8, 2013 (DE) ...................... 10 2013 013 278.9

(51) Int. Cl.
*A61M 21/00* (2006.01)
*A61F 11/00* (2006.01)
(Continued)

(52) U.S. Cl.
CPC .......... *A61M 21/00* (2013.01); *A61B 5/4836* (2013.01); *H04R 25/75* (2013.01); *A61B 5/12* (2013.01);
(Continued)

(58) Field of Classification Search
CPC .......... A61M 21/00–02; A61B 5/4836; A61B 5/04845; A61B 5/12–128; A61B 5/38; H04R 25/00–75; A61F 11/00
See application file for complete search history.

(56) References Cited

U.S. PATENT DOCUMENTS

| 4,883,067 A | 11/1989 | Knispel et al. |
| 2005/0113871 A1 | 5/2005 | Choy |
| 2015/0297444 A1 | 10/2015 | Tass et al. |

FOREIGN PATENT DOCUMENTS

| DE | 10 2008 015259 A | 9/2004 |
| DE | 10 2010 016 461 A | 4/2010 |

(Continued)

OTHER PUBLICATIONS

A.N. Siichenko, I. Adamchic, C, Hauptmann, P.A. Tass: "Impact of acoustic coordinated reset neuromodulation on effective connectivity in a neural network of phantom sound", Neuroimage 77, 133-147 (2013).

(Continued)

*Primary Examiner* — Thaddeus B Cox
(74) *Attorney, Agent, or Firm* — Arent Fox LLP

(57) ABSTRACT

An apparatus for stimulating neurons that includes a stimulation unit for applying pulse-like tones, a measuring unit for picking up measurement signals that render neural activity by the stimulated neurons, a control. The control unit applies a first pulse train having varied pitch, takes the measurement signals picked up in response to the first pulse train to select a first pitch range or pitch in which there is phase synchronization between the pulse train and the neural activity, actuates the stimulation unit to apply two phase-shifted second pulse trains, the pitch of the pulse trains being varied in opposite directions and a pitch starting value of the second pulse trains based on first pitch range or pitch that is used to select a second pitch range or pitch resulting in minimum amplitude of the neural activity.

17 Claims, 7 Drawing Sheets

(51) Int. Cl.
- *A61B 5/12* (2006.01)
- *A61B 5/38* (2021.01)
- *H04R 25/00* (2006.01)
- *A61B 5/00* (2006.01)

(52) U.S. Cl.
CPC .............. *A61B 5/38* (2021.01); *A61F 11/00* (2013.01); *A61M 2021/0027* (2013.01); *A61M 2230/10* (2013.01)

(56) References Cited

FOREIGN PATENT DOCUMENTS

| DE | 10 2012 002438 A | 6/2013 |
|---|---|---|
| WO | WO 2011127817 A | 4/2010 |

OTHER PUBLICATIONS

Au Huang, Ne et al,: "A confidence limit for the empirical mode decomposition and Hilbert spectral analysis", Proceedings of the Royal Society of London Series A (2003), vol. 459, 2317-2345.

B. Lysyansky et al, "Desynchronizing anti-resonance effect of m: n ONOFF coordinated reset stimulation", Journal of Neural Engineering, Institute of Physics Publishing. Bristol. GB, vol. 8, No. 3, May 10, 2011 (May 10, 2011), page 36019. XP020206979, ISSN: 1741-2552. DOI: 10.1088/1741-2560/8/3/036019.

Békésy G. v.: "A new audiometer", Acta oto-laryngol. (Stockh.) 35 (1947) 411.

E. Batschelet: "Circular Statistics in Biology", Academic Press, London (1981).

Huang N.E. et al., "The empirical mode decomposition and the Hilbert spectrum for nonlinear and non-stationary time series analysis". Proc R Soc A: Math Phys Eng Sci 454:903-995 (1998)

I. Adamchic, T. Toth, C. Hauptmann, P.A. Tass: "Reversing pathalogically increased EEG power by acoustic CR neuromodulation", Human Brain Mapping (in press).

International Preliminary Report for PCT/EP2014/066611, dated Feb. 11, 2016.

Lehnhardt E., Laszig R.: "Praxis der Audiometrie", Thieme, Stuttgart, 9 Auflage, 2009, pp. 91-95. |This document describes a Békésy audiometer to continuously scan the auditory threshold over the frequency axis.

M.G. Rosenblum, A.S. Pikovsky, C. Schàfer, J. Kurths, P.A. Tass: "Phase Synchronization: From Theory to Data Analysis. In Moss F, (Ed.)", Handbook of Biological Physics, Elsevier (2000).

N. H. Kuiper; "Tests concerning random points in a circle", Proc. K. Ned. Akad. Wet., Ser. A: Math. Sci. 63, 38 (1960).

P. Landa: "Nonlinear Oscillations and Waves in Dyanmical Systems", Kluwer Academic Publishers, Dordrecht-Boston-London (1996), Chapter 23.

P. Tass, M.G. Rosenblum, J. Weufe, J. Kurths, A. Pikovsky, J. Volkmann, A. Schnitzler, and H.-J. Freund; "Detection of nm Phase Locking from Noisy Data: Application to Magnetoencephalography", Phys. Rev. Lett. 81 (15), 3291-3294.

P.A. Tass, L Adamchic, H.-J. Freund, T. von Stackelberg, C. Hauptmann: "Counteracting tinnitus by acoustic coordinated reset neuromodulation", Restorative Neurology and Neuroscience 30, 137-159.

P.A. Tass: "Transmission of simulus-locked responses in two coupled phase oscillators", Phys. Rev. E 69, 051909-1-24 (2004).

Taylor, Wayne (2000a). "Change-Point Analyzer 2.0 shareware program", Taylor Enterprises, Libertyville, Illinois. Web: http://www.variation.com/cpa (Software).

"EEG phase synchronization and information flow during audio-visual stimulation", Michal Teplan, et al., 2010 3rd International Symposium on Applied Sciences in Biomedical and Communication Technologies (ISRAEL 2010).

Chinese Office Action for corresponding Chinese Application No. 2018073101381910 dated Aug. 3, 2018.

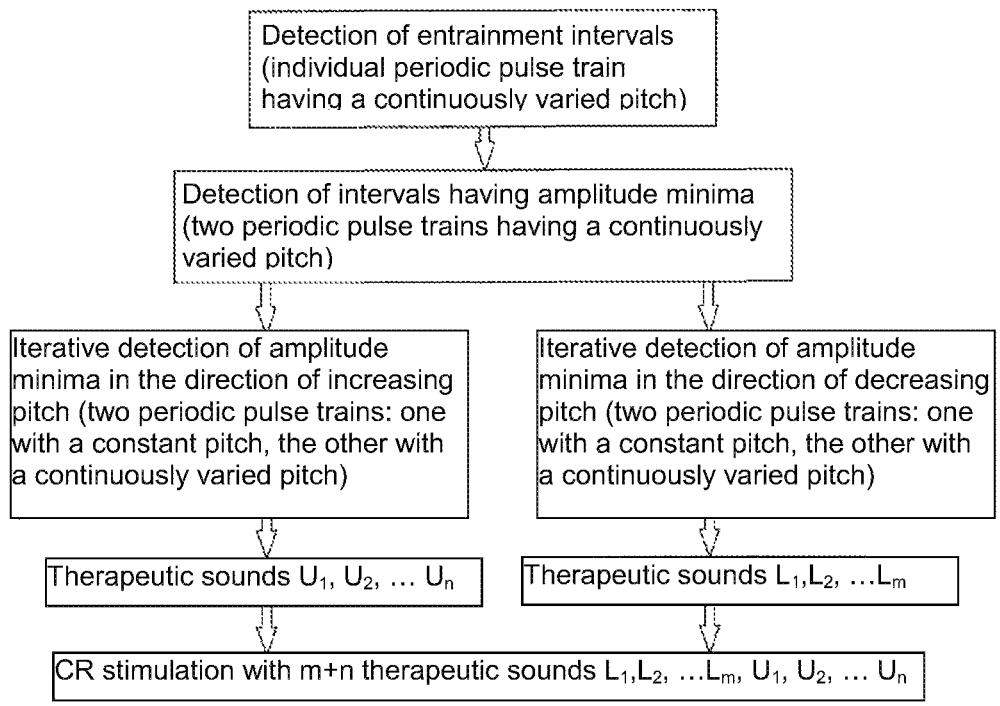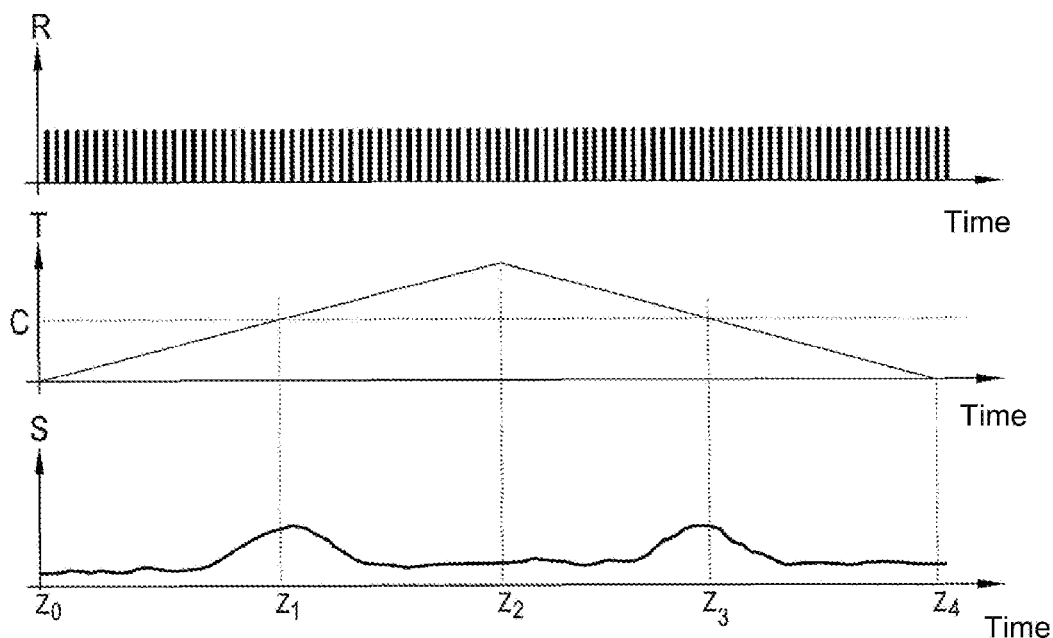

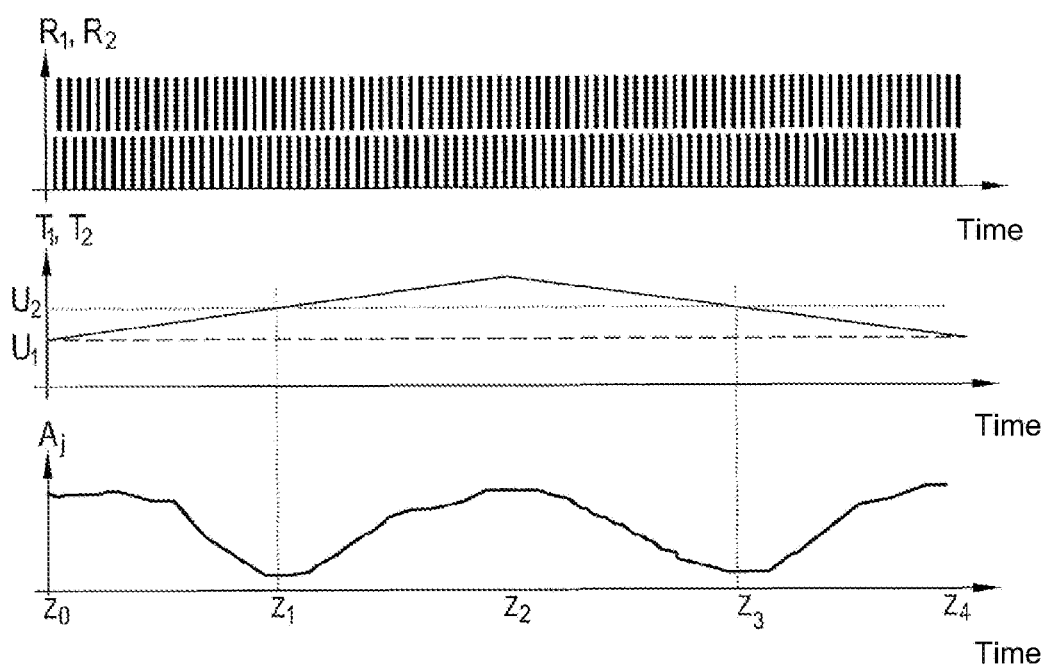
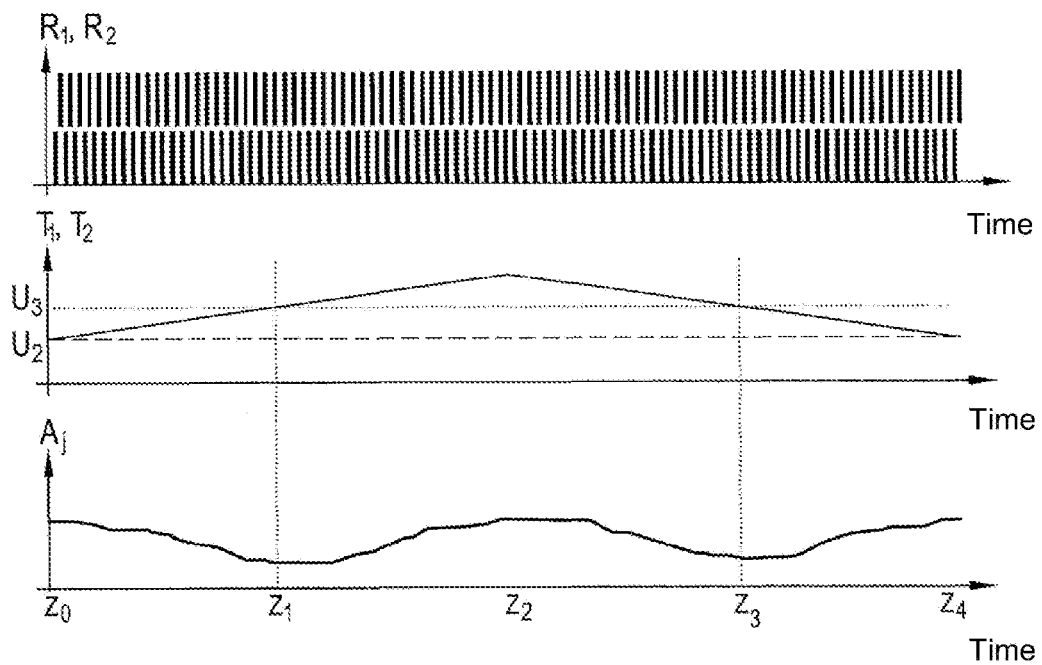

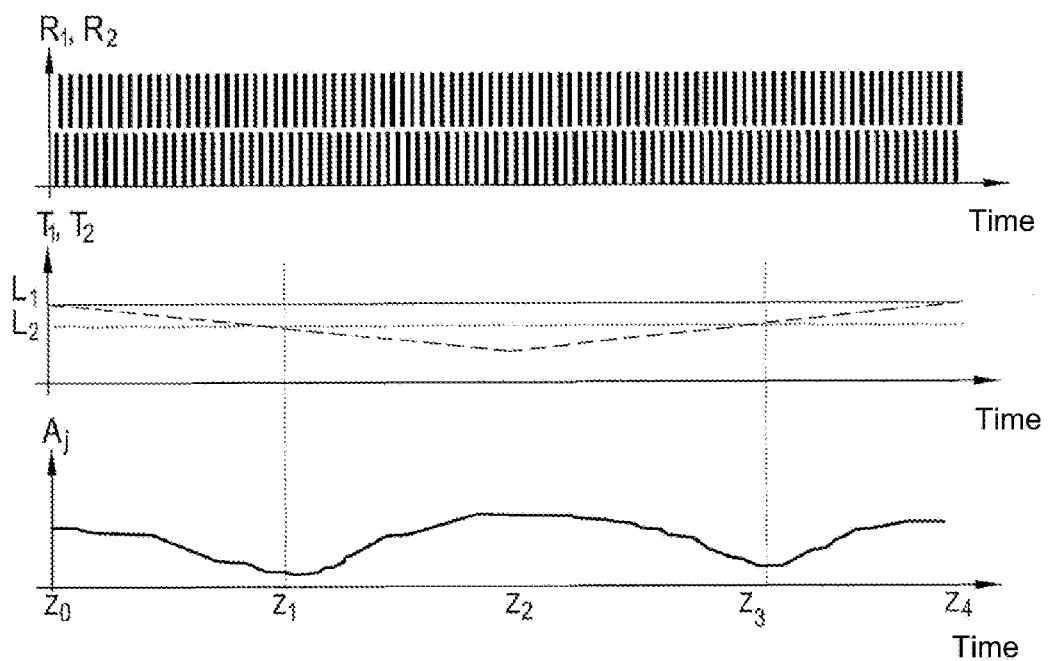
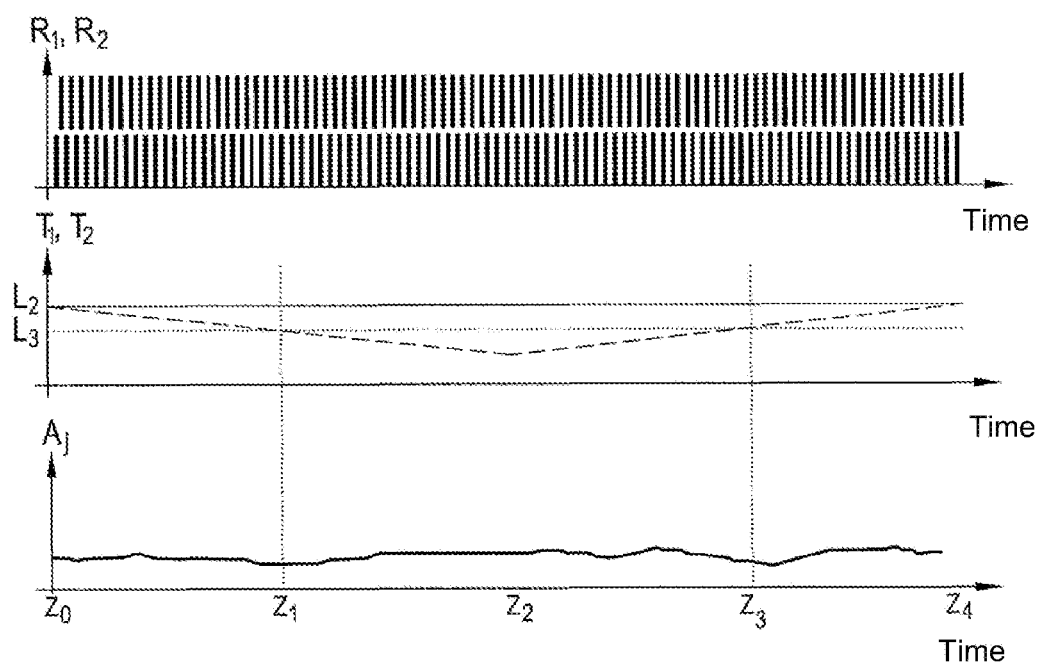

APPARATUS AND METHOD FOR CALIBRATING ACOUSTIC DESYNCHRONIZING NEUROSTIMULATION

CROSS-REFERENCE TO RELATED APPLICATIONS

This application is divisional application of U.S. application Ser. No. 14/910,412, filed Feb. 5, 2016, now issued as U.S. Pat. No. 10,328,233 on Jun. 25, 2019, which is a U.S. National Stage of International Application No. PCT/EP2014/066611, filed Aug. 1, 2014 and claims the benefit thereof. The International Application claims the benefits of German application No. 10 2013 013278.9, filed Aug. 8, 2013, the contents of each of which are incorporated by reference herein in their entirety.

FIELD OF TECHNOLOGY

The invention relates to an apparatus and to a method for calibrating acoustic desynchronizing neurostimulation.

BACKGROUND

Nerve cell structures in circumscribed regions of the brain are pathologically, e.g. excessively synchronously, active in patients with neurological diseases such as tinnitus, depression, obsessive compulsive disorders, ADHS or schizophrenia. In this case, a large number of neurons synchronously form action potentials; the participating neurons fire excessively synchronously. In a healthy person, in contrast, the neurons fire with a different quality, i.e. in an uncorrelated manner, in these brain sectors.

Acoustic coordinated reset (CR) stimulation was developed for the treatment of chronic subjective tinnitus; it directly counteracts pathologically synchronous neural activity (P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012); I. Adamchic, T. Toth, C. Hauptmann, P. A. Tass: Reversing pathologically increased EEG power by acoustic CR neuromodulation. Human Brain Mapping (in press)) and can also normalize the pathologically modified interactions (so-called effective connectivity) between different brain areas (A. N. Silchenko, I. Adamchic, C. Hauptmann, P. A. Tass: Impact of acoustic coordinated reset neuromodulation on effective connectivity in a neural network of phantom sound. Neuroimage 77, 133-147 (2013)). The acoustic CR stimulation is characterized by therapeutic effectiveness and safety (P. A. Tass, I. Adamchic, H.-J. Freund, T. von Stackelberg, C. Hauptmann:

Counteracting tinnitus by acoustic coordinated reset neuromodulation. Restorative Neurology and Neuroscience 30, 137-159 (2012)).

It is of key importance for the effectiveness of the acoustic CR stimulation that the different stimulation sites actually lie in the neural population to be stimulated. There is no imaging process which could determine the spatial extent of pathological neural synchronization. The CR therapeutic sounds are thus not determined by means of an objective method, but rather by means of an audiometric procedure which is based on psychoacoustics and is thus deficient to a different degree depending on the patient. The dominant tinnitus frequency is first determined audiometrically in the audiometric adaptation of the CR sounds. This typically does not work with patients having noise tinnitus, but rather only with patients having tonal tinnitus. The pitches of the CR therapeutic sounds are rigidly predefined (P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012)). In a second step, the loudness of the therapeutic sounds is balanced with rigidly predefined pitches (which are e.g. in the range from 77% up to 140% of the dominant pitch of the tinnitus) (i.e. the loudness of the CR therapeutic sounds is set to the same subjective loudness where possible).

Approximately 25% of patients having tonal tinnitus do not respond to this therapy (P. A. Tass, I. Adamchic, H.-J. Freund, T. von Stackelberg, C. Hauptmann: Counteracting tinnitus by acoustic coordinated reset neuromodulation. Restorative Neurology and Neuroscience 30, 137-159 (2012)). This approximately corresponds to the percentage of patients having tonal tinnitus who cannot make any pitch balance between their tinnitus and a computer comparison sound. In addition the CR treatment in its current form (i.e. with the above-described audiometric adaptation of the CR sounds) is only suitable with limitations for patients having noise tinnitus within a narrow band and is not suitable for patients having noise tinnitus within a broad band. On the one hand, an (audiometrically determinable) dominant tinnitus frequency is lacking and, on the other hand, the rigidly predefined arrangement of the pitches of the CR therapeutic sounds (e.g. in the range from 77% up to 140% of the dominant pitch of the tinnitus) is typically not suitable since the pathologically synchronous focus underlying the noise tinnitus e.g. has a different extent in the central audiometric system than in the case of tonal tinnitus.

An analog situation results in the case of the treatment of other brain diseases such as ADHS, depression, obsessive compulsive disorders or schizophrenia with acoustic CR stimulation. The choice of the suitable CR therapeutic sounds up to now has only been able to be carried out audiometrically or using trial and error. Time-consuming trial and error does not guarantee the ideal effectiveness of the non-invasive CR therapy since, on the one hand, not all possible stimulation sites in the brain are systematically developed and tested and, on the other hand, the patients are stressed by long examinations so that the cooperation of the patients naturally suffers and the results of the test become worse.

SUMMARY

Calibration procedures were previously carried out by audiometric/psychophysical adaptations (e.g. in acoustic CR stimulation for treating tinnitus). It is the underlying object of the invention to provide an apparatus with which an objective calibration, which can be performed at sufficient speed, can be carried out.

The object is satisfied in that the subjective measurement (e.g. audiometric adaptation with acoustic CR stimulation) is replaced with an objective examination which can be carried out at sufficient speed using the apparatus in accordance with the invention. The latter allows an electrophysiologically based measurement of the evoked responses of the brain which can be carried out at sufficient speed for the calibration of the ideal stimulation parameters and stimulation sites.

The object is satisfied using the following apparatus in accordance with the invention: the apparatus in accordance with the invention comprises (i) a measuring unit having non-invasive or (less preferably) invasive sensors for electrophysiological measurement of the pathological neural activity or of an activity (e.g. muscle activity) representing it or correlating sufficiently closely with it; (ii) a stimulation unit for applying acoustic stimuli; and (iii) a control and analysis unit.

BRIEF DESCRIPTION OF THE DRAWINGS

The invention will be described in more detail in the following in an exemplary manner with reference to the drawings.

FIG. 1 illustrates a flowchart of the routine of the procedure in accordance with the invention in the variant without a centrally arranged therapeutic sound (so-called central sound).

FIG. 2 illustrates a chart showing the detection of entrainment intervals (individual periodic pulse train with a continuously varied pitch).

FIG. 4 illustrates a chart showing the application of two constant periodic out-of-phase pulse trains, wherein the pitch ($U_2$) of only one of the two pulse trains is continuously varied in a rising and then falling manner.

FIG. 5 illustrates a chart showing the application of two constant periodic out-of-phase pulse trains, wherein the pitch ($U_3$) of only one of the two pulse trains is continuously varied in a rising and then falling manner.

FIG. 6 illustrates a chart showing the application of two constant periodic out-of-phase pulse trains, wherein the pitch ($L_2$) of only one of the two pulse trains is continuously varied in a falling and then rising manner.

FIG. 7 illustrates a chart showing the application of two constant periodic out-of-phase pulse trains, wherein the pitch ($L_3$) of only one of the two pulse trains is continuously varied in a falling and then rising manner.

FIG. 9 and FIG. 2 are accordingly identical.

DETAILED DESCRIPTION

Provision can by all means be made that the individual components of the apparatus in accordance with the invention, in particular the measuring unit, the stimulation unit and the control and analysis unit, are constructionally separate from one another. The apparatus in accordance with the invention can therefore also be understood as a system.

The apparatus in accordance with the invention can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neural synchronization.

The aforesaid diseases can be caused by a disorder of the bioelectric communication of neural assemblies which are connected in specific circuits. In this respect, a neural population continuously generates pathological neural activity and possibly a pathological connectivity associated therewith (network structure). In this respect, a large number of neurons synchronously form action potentials, i.e. the participating neurons fire excessively synchronously. In addition, there is the fact that the pathological neural population has an oscillatory neural activity, i.e. the neurons fire rhythmically. In the case of neurological or psychiatric diseases, the mean frequency of the pathological rhythmic activity of the affected neural assemblies lies approximately in the range from 1 to 30 Hz, but can also be outside this range. In healthy people, the neurons fire qualitatively differently, however, e.g. in an uncorrelated manner.

Figure 11:
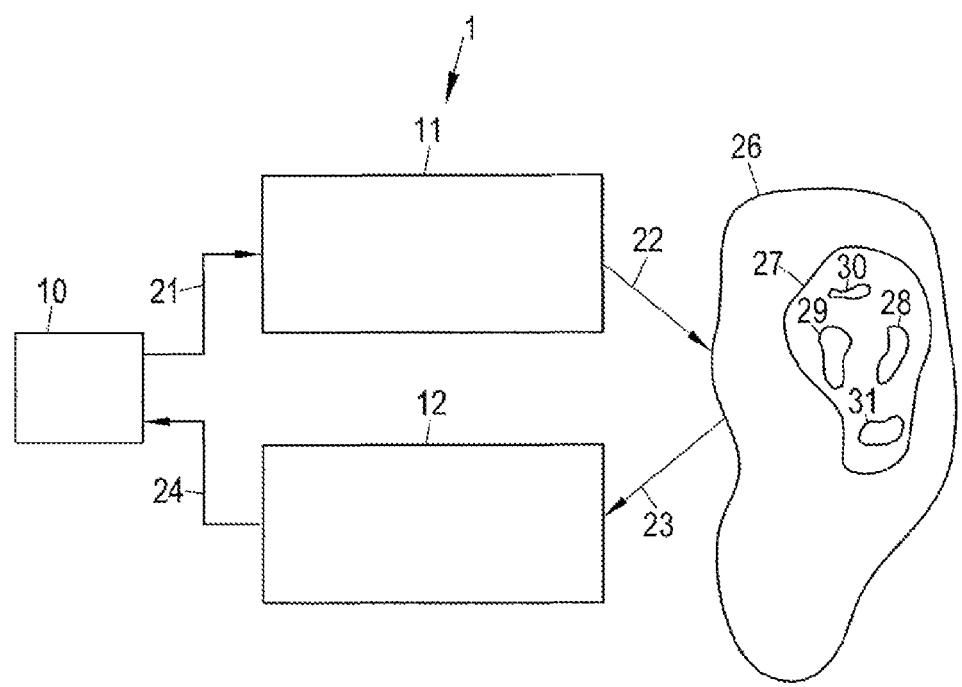
FIG. 11 illustrates an apparatus for calibrating acoustic desynchronizing neurostimulation according to an embodiment.

An apparatus 1 for calibrating acoustic desynchronizing neurostimulation is shown schematically as an embodiment of the invention in FIG. 11. The apparatus 1 comprises a control and analysis unit 10, a stimulation unit 11 and a measuring unit 12. During the operation of the apparatus 1, the control and analysis unit 10 inter alia carries out a control of the stimulation unit 11. For this purpose, the control and analysis unit 10 generates control signals 21 which are received by the stimulation unit 11. The stimulation unit 11 generates stimuli 22, i.e. sounds, with reference to the control signals 21 and they are administered to a patient. The stimulation unit 11 and in particular also the control and analysis unit 10 are non-invasive units, i.e. they are located outside the body of the patient during the operation of the apparatus 1 and are not surgically implanted in the body of the patient.

The stimulation effect achieved by the sounds 22 is monitored with the aid of the measuring unit 12. The measuring unit 12 records one or more measured signals 23 measured at the patient, converts them as required into electrical signals 24 and supplies them to the control and analysis unit 10. The neural activity in the stimulated target zone or in a zone associated with the target zone can in particular be measured by means of the measuring unit 12, with the neural activity of this zone correlating sufficiently closely with the neural activity of the target zone (e.g. muscle activity). The control and analysis unit 10 processes the signals 24, e.g. the signals 24 can be amplified and filtered, and analyzes the processed signals 24. The control and analysis unit 10 in particular controls the stimulation unit 11 with reference to the results of this analysis. The control and analysis unit 10 can, for example, include a processor (e.g. a microcontroller) for carrying out its work.

The apparatus 1 is shown during a CR stimulation in FIG. 11. At least one neural population 27 in the brain 26 of the patient has a pathologically synchronous and oscillatory neural activity. The stimulation unit 11 administers the sounds 22 to the patient in this manner which are received via the patient's ears and are forwarded from there via the nervous system to the pathologically active neural population 27 in the brain 26. The sounds 22 are designed such that the pathologically synchronous activity of the neural population 27 is desynchronized. A lowering of the coincidence rate of the neurons effected by the stimulation can result in a lowering of the synaptic weights and thus in an unlearning of the tendency to produce pathologically synchronous activity.

Acoustic stimuli are converted into nerve impulses in the inner ear and are forwarded via the acoustic nerve to the auditory cortex. A specific portion of the auditory cortex is activated on the acoustic stimulation of the inner ear at a specific frequency due to the tonotopic arrangement of the auditory cortex.

The stimulation unit 11 can accordingly separately stimulate different regions of the brain 26 in that the applied stimuli 22 are forwarded via neural conductors to different target zones which lie in the brain 26. The target zones can be stimulated with possibly different and/or time-offset stimuli 22 during the CR stimulation.

In the CR stimulation, stimuli 22 which effect a reset of the phase of neural activity of the stimulated neurons in the neural population 27 are administered to the neural population 27 which has a pathologically synchronous and oscillatory activity. The phase of the stimulated neurons is set to or close to a specific phase value, e.g. 0°, independently of the current phase value by the reset (it is not possible in practice to set a specific phase value exactly; however, this is also not required for a successful CR stimulation). The phase of the neural activity of the pathological neural population 27 is thus controlled by means of a direct stimulation. Since it is furthermore possible to stimulate the pathological neural population 27 at different sites, the phase of neural activity of the pathological neural population 27 can be rest at the different stimulation sites at different points in time. As a result, the pathological neural population 27 whose neurons were previously synchronous and active at the same frequency and phase is split into a plurality of subpopulations which are shown schematically in FIG. 11 and are marked by the reference numerals 28, 29, 30 and 31 (four subpopulations are shown by way of example here). Within one of the subpopulations 28 to 31, the neurons are still synchronous after the resetting of the phase and also still fire at the same pathological frequency, but each of the subpopulations 28 to 31 has the phase with respect to their neural activity which was enforced by the stimulation stimulus. This means that the neural activities of the individual subpopulations 28 to 31 still have an approximately sinusoidal curve at the same pathological frequency, but different phases, after the resetting of their phases.

Due to the pathological interaction between the neurons, the state with at least two subpopulations generated by the stimulation is unstable and the total neural population 27 fast approaches a state of complete desynchronization in which the neurons fire without correlation. The desired state i.e. the complete desynchronization, is thus not immediately present after the time-offset (or phase-shifted) application of the phase-resetting stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It also has the effect that a division of an overall population 27 into subpopulations 28 to 31 with different phases is followed by a desynchronization. In contrast to this, no desynchronization would take place without a pathologically increased interaction of the neurons.

Furthermore, a reorganization of the connectivity of the disturbed neural networks can be achieved by the CR stimulation so that long-lasting therapeutic effects can be brought about. The obtained synaptic conversion is of great importance for the effective treatment of neurological or psychiatric diseases.

1. Measuring unit with sensors: The sensors measure signals which make it possible to detect an adequate data analysis, in particular (a) a phase locking, i.e. a phase synchronization, between a pulse train which is strictly periodic (with respect to the timing), on the one hand, and the phase of pathologically oscillatory activity, on the other hand, and (b) a decrease or increase in the amplitude of the pathological oscillatory activity, that is e.g. electroencephalography (EEG) signals, magnetocencephalography (MEG) signals, local field potentials (LFP).

Invasive sensors: implanted electrodes, e.g. epicortical electrodes, epidural electrodes, deep electrodes Non-invasive sensors: (non-implanted) EEG electrodes (preferable equipment variant), MEG sensors (SQUIDS). Less preferred: indirect measurement of the neural activity by measuring the accompanying muscle activity using electromyography (EMG).

2. Stimulation unit: This is an apparatus for acoustic stimulation with which sound signals are administered at one side or at both sides and different signals are administered over both sides for stimulation purposes (e.g. sounds, tones, noises) over one or both ears of a patient or subject.

3. Control and analysis unit: This unit amplifies the measured signals. The control and analysis unit can be present in a fixed, wired state, for example as a computer or controller or the like. It in particular has data analysis processes for determining the characteristic of a phase synchronization between a periodic stimulus and a neural rhythm to be examined, e.g.:

A stimulus is applied at the times $\tau_1, \tau_2, \ldots \tau_M$. It is a periodic stimulus sequence, i.e. the stimulation period (i.e. period of stimulus sequence) is constant: $T_{stim} = \tau_{j+1} - \tau_j$ for all $j=1, 2, \ldots, M-1$, where M stands for the number of the individual stimuli. The associated stimulation frequency, i.e. repetition rate is $F_{stim} = 1/T_{stim}$.

The stimulation frequency $F_{stim}$ is selected in accordance with the prior knowledge familiar to the skilled person with respect to the pathological frequency bands characteristic for the respective disease (that is in agreement with the pathological rhythms which should be desynchronized using CR) or is adapted by means of feedback by measurement of the pathological neural activity to be desynchronized via sensors and a determination of the frequency peak in the pathological frequency band familiar to the skilled person.

Phase of periodic stimulus: The phase of the periodic stimulus frequency is $\varphi_1(t) = 2\pi(t-\tau_1)/T_{stim}$ (see e.g. M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)). The phase thus selected disappears when the first stimulus is applied: $\varphi_1(t)=0$. Alternatively, a phase shift can also be "built in" which does not change anything in the results and also does not bring about any advantages. A phase shift can be "built in" in that either a different start time is selected $\varphi_1(t)=2\pi(t-\xi)/T_{stim}$, where $\xi \neq \tau_1$ and $\xi$=const, or in that a phase shift $\vartheta$ is explicitly added $\varphi_1(t)=2\pi(t-\tau_1)/T_{stim}+\vartheta$, where $\vartheta$=const.

Phase of neural oscillation: $\varphi_2$, the phase of the neural rhythm to be examined is determined by means of Hilbert transformation from the signal which is determined by means of band pass filtering or empirical mode decomposition and which represents the pathological oscillatory activity. The empirical mode decomposition allows, in contrast to band pass filtering, a parameter-independent determination of physiologically relevant modes in different frequency ranges (Huang N. E. et al. (1998) The empirical mode decomposition and the Hilbert spectrum for nonlinear and non-stationary time series analysis. Proc R Soc A: Math Phys Eng Sci 454:903-995). The combination of empirical mode decomposition with a subsequent Hilbert transformation is called Hilbert-Huang transformation (AU Huang, N E et al. "A confidence limit for the empirical mode decomposition and Hilbert spectral analysis", Proceedings of the Royal Society of London Series A (2003), VOL. 459, 2317-2345). In addition to the instantaneous (time-dependent) phase $\varphi_2(t)$ of the neural oscillation to be examined, its instantaneous (time-dependent) amplitude A(t) is additionally obtained in this manner.

Phase synchronization between stimulus and neural rhythm:

We consider the n:m phase difference between the stimulus and the neural rhythm $\psi_{n,m}(t)=n\varphi_1(t)-m\varphi_2(t)$, where n and m are small whole numbers, for example from the range 1 to 5. In this manner, the phase synchronization between the stimulus and a neural rhythm can be examined in different frequency bands. I.e. to examine the effect of the stimulation on neural rhythms, it is not necessary to restrict oneself to the rhythm which is in the same frequency range as the stimulus frequency (n=m=1). The n:m phase difference modulo $2\pi$ is $\phi_{n,m}(t)=[n\varphi_1(t)-m\varphi_2(t)]_{mod\ 2\pi}$.

n:m phase synchronization:

The n:m phase difference modulo $2\pi$ is determined, ascertained inter alia by the sampling rate, at the times $t_1, t_2, \ldots, t_N$. We herewith obtain the associated distribution of $\phi_{n,m}$ which is $\{\phi_{n,m}(t)\}_{j=a}^b$. The distribution can include all measured values of $\phi_{n,m}$ ($a=t_1$, $b=t_N$) or only a subgroup ($a>t_1$ and/or $b<t_N$) in order e.g. to exclude transient effects from the analysis. For this purpose, e.g. the first approximately 10 stimuli are removed from the analysis.

If there is no n:m phase synchronization, the distribution of the n:m phase difference modulo $2\pi$ is an equal distribution (or comes sufficiently close thereto). In contrast to this, the n:m phase synchronization is characterized by the occurrence of one or more cluster points of $\phi_{n,m}(t)$ (P. Tass, M. G. Rosenblum, J. Weule, J. Kurths, A. Pikovsky, J. Volkmann, A. Schnitzler, and H.-J. Freund: Detection of n:m Phase Locking from Noisy Data: Application to Magnetoencephalography. Phys. Rev. Lett. 81 (15), 3291-3294 (1998); M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)).

The occurrence of an n:m phase synchronization can be determined by means of different variables. Examples will be shown in the following:

(i) If the distribution of $\phi_{n,m}$ has a (single) cluster value, the circular mean value of this distribution can be calculated:

$$S_{n,m} = \left| \frac{1}{b-a+1} \sum_{l=a}^{b} \exp[i\phi_{n,m}(t_l)] \right|,$$

where $0 \leq S_{n,m} \leq 1$, and an equal distribution results in $S_{n,m}=0$, whereas a perfect phase synchronization is characterized by $S_{n,m}=1$ (M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)). The disadvantage of this synchronization index is that it typically does not deliver any sensible results if the distribution $\{\phi_{n,m}(t)\}_{j=a}^b$ has more than one cluster value. If e.g. it has two out-of-phase cluster values, a value of $S_{n,m}$ close to zero results.

(ii) A synchronization index should therefore additionally (or exclusively) be calculated which delivers reliable results independently of the number of cluster values. For this purpose, the Kuiper test, the circular variant of the Kolmogorov-Smirnov test (E. Batschelet, Circular Statistics in Biology (Academic Press, London, 1981); N. H. Kuiper: Tests concerning random points in a circle. Proc. K. Ned. Akad. Wet., Ser. A: Math. Sci. 63, 38 (1960); P. A. Tass: Transmission of stimulus-locked responses in two coupled phase oscillators. Phys. Rev. E 69, 051909-1-24 (2004)), is used to determine the probability with which the distribution $\{\phi_{n,m}(t)\}_{j=a}^b$ is an equal distribution, A P value is then obtained which is the smallest significance level at which the zero hypothesis (that the observed distribution $\{\phi_{n,m}(t)\}_{j=a}^b$ is an equal distribution) can be rejected. If $\{\phi_{n,m}(t)\}_{j=a}^b$ is an equal distribution P=1 results. If, in contrast, $\{\phi_{n,m}(t)\}_{j=a}^b$ has a single, considerably pronounced cluster value, a P value close to zero is obtained.

(iii) A further possibility is an n: m synchronization index $\rho_{n,m}$ based on the Shannon entropy of the distribution $\{\phi_{n,m}(t)\}_{j=a}^b$. An estimate $p_k$ of the distribution $\{\phi_{n,m}(t)\}_{j=a}^b$ produces $$\rho_{n,m} = \frac{S_{max} - S}{S_{max}},$$

where $S=-\Sigma_{k=1}^L p_k \ln p_k$. The maximum entropy is $S_{max}=\ln L$, where L is the number of bins. $p_k$ is the relative frequency with which $\phi_{n,m}$ is found in the k th bin (P. Landa: Nonlinear Oscillations and Waves in Dynamical Systems. Kluwer Academic Publishers, Dordrecht-Boston-London, 1996). $0 \leq \rho_{n,m} \leq 1$ applies due to the normalization. With an equal distribution, that is with a complete lack of an n:m phase synchronization, $\rho_{n,m}=0$ results, whereas a perfect n:m phase synchronization results in a Dirac-like distribution (i.e., all values of $\phi_{n,m}$ are in the same bin) so that $\rho_{n,m}=1$. In comparison with the n:m synchronization index listed under (ii) and based on the Kuiper test, the n:m synchronization index $\rho_{n,m}$ based on the Shannon entropy has the disadvantage that its value depends on the exact position of the cluster value with more pronounced cluster values of the distribution so that artificial oscillations result with a cyclic shift of the cluster value in the interval $[0,2\pi]$ (P. A. Tass: Transmission of stimulus-locked responses in two coupled phase oscillators. Phys. Rev. E 69, 051909-1-24 (2004)).

In addition to the stimulation-induced effects on the phase $\varphi_2(t)$ of the neural rhythm and thus the n:m phase difference $\phi_{n,m}$ stimulation-induced effects on the amplitude $A(t)$ of the neural rhythm are also examined. It is not only a question of whether the stimulation brings the neural rhythm in cycle in an n:m relationship, but rather whether the stimulation also changes the degree of the synchronization of the neurons underlying the neural rhythm. An increase in the synchronization within the stimulated neural population results in an increase of $A(t)$. Conversely, a decrease in the synchronization within the neural population underlying the neural rhythm produces a decrease of $A(t)$. Measurements in a comparison interval (e.g. before administering the stimulation) thus have to be carried out for the evaluation of the amplitude effects. Alternatively, amplitude effects can also simply be determined by an analysis of the power spectral density—of a predefined frequency band typical for the disease and familiar to the skilled person or of one or more empirical modes extracted from the data (see above).

2 variants inter alia result with respect to the embodiment of the invention:

(I) Continuous (or Small-Step) Variation of One (or More) Stimulus Property/Properties During the Application of a Strictly Periodic Pulse Train.

The essential characteristic of this process is that one or more stimulus parameters (e.g. the pitch) are varied while a periodic pulse train is applied.

Example: EEG-Based Calibration of the CR Therapeutic Sounds for the Acoustic CR Stimulation for Treating Tinnitus as Well as Further Neurological and Psychiatric Diseases (e.g. ADHS, Obsessive Compulsive Disorders, Depression)

Subvariant I.1: Determining the CR Therapeutic Sounds without Central Sound

This is the preferred variant which from the start aims for a symmetrical arrangement of the therapeutic sounds around the center of the region which is characterized by a strong entrainment (and which corresponds to the focus or focal centers of the pathological synchronization in the central nervous system). The procedure of this process is shown schematically in FIG. 1.

FIG. 1 shows a flowchart of the routine of the procedure in accordance with the invention in the variant without a centrally arranged therapeutic sound (so-called central sound).

FIG. 2 shows the detection of entrainment intervals (individual periodic pulse train with a continuously varied pitch). The x axis is the time axis in all three illustrations. The topmost illustration schematically shows the extent of the acoustic stimuli. A single black bar stands for a pure sound of a pitch T which is folded using a Hamming window or (less preferably) with a cosine function or another, preferably smooth envelope which typically restricts the time extent of the sound). The middle illustration schematically shows how the pitch T of the periodically applied sound is continuously varied. The bottom illustration schematically shows the extent of the synchronization index (briefly marked as S in the illustration), that is e.g. the phase synchronization index $S_{n,m}$ (see above).

I.1.a Detection of Entrainment Intervals

The frequency ranges (i.e. pitch ranges) which have an n:m phase synchronization between the pulse train and the brain oscillation (that is an n:m entrainment) (FIG. 2) are first detected by means of a pulse train which is constant (with respect to the time structure) and which has a pitch which changes continuously (e.g. is varied in rising and falling directions). With an n:m phase synchronization, the pathological neural oscillation is influenced by the stimulation such that m periods of pathological oscillation come to lie in n periods of the periodic stimulus (P. Tass, M. G. Rosenblum, J. Weule, J. Kurths, A. Pikovsky, J. Volkmann, A. Schnitzler, and H.-J. Freund: Detection of n:m Phase Locking from Noisy Data: Application to Magnetoencephalography. Phys. Rev. Lett. 81 (15), 3291-3294 (1998); M. G. Rosenblum, A. S. Pikovsky, C. Schäfer, J. Kurths, P. A. Tass: Phase Synchronization: From Theory to Data Analysis. In: Moss F. (Ed.): Handbook of Biological Physics, Elsevier (2000)). The phase dynamics of a pathological neural oscillation can be influenced particularly efficiently and with a low intensity (loudness) in the pitch ranges in which a pronounced phase synchronization can be detected. The schematic results shown in FIG. 2 can be evaluated by visual inspection, on the one hand. They are preferably automatically evaluated by the apparatus in accordance with the invention. E.g. the associated parts of the curves of the synchronization index (S in the bottommost illustration of FIG. 2) can be averaged which belong to the rising and falling pitch extent:

$\bar{S}(t)=[S(t)+S(z_4-t)]/2$, where $t\in[z_0,z_2]$, with the rising and falling of the pitches extending at the same speed, that is symmetrically in time, (see middle illustration in FIG. 2), where $z_4-z_2=z_2-z_0$. The time axis t can be simply converted into a pitch axis g over time in the case of a linear rise or fall of the pitch. If $g_0$ and $g_2$ are the pitches which are used at the times $t_0$ and $t_2$ for the pulse train, the conversion formula is $\bar{S}(g)=\bar{S}[z_0+(z_2-z_0)\,(g-g_0)/(g_2-g_0)]$, where $g\in[g_0,g_2]$. The acoustic coordinated reset stimulation is sufficiently robust with respect to variations of the pitch of the CR therapeutic sounds so that the maximum of $\bar{S}$ does not have to be detected with an inappropriate (i.e. unrealistic) precision. $\bar{S}(g)$ can rather simply be filtered in a low pass; the curve hereby obtained is designated as $\bar{S}_T(g)$. The parameters of the low pass filter should allow the maximum to be determined simply. The simple shifts of the pitch at which the maximum of $\bar{S}_T(g)$ comes to lie arising by a variation of the parameters of the low pass filter do not influence the therapeutic success. The pitch at which the maximum of $\bar{S}_T(g)$ is detected, is called the central sound C.

$$\bar{S}_T(C) = \max_{g\in[g_0,g_2]} \{\bar{S}_T(g)\}.$$

If $\bar{S}_T(g)$ should have a plurality of (more precisely K different) local maxima (with associated pitches, i.e. central sounds $C_1, C_2, \ldots, C_K$) for $g \in [g_0, g_2]$, there are different embodiments as to how to proceed in this respect, e.g.:

(i) Only the global maximum (located at the pitch C) for $g \in [g_0, g_2]$ is considered, i.e.

$$\bar{S}_T(C) = \max_{j \in [1, \ldots, K]} \{\bar{S}_T(C_j)\}.$$

(ii) To consider secondary peaks of a main maximum or "multi-jagged" main peaks, the spread $\Delta S$ of $\bar{S}_T(g)$ für $g \in [g_0, g_2]$ is calculated:

$$\Delta S = \max_{g \in [g_0, g_2]} \{\bar{S}_T(g)\} - \min_{g \in [g_0, g_2]} \{\bar{S}_T(g)\}.$$

Only sufficiently pronounced local maxima should be considered for the further evaluation. This can e.g. be achieved in that only local maxima are considered which e.g. exceed half the spread, that is which are larger than $$\sigma = \min_{g \in [g_0, g_2]} \{\bar{S}_T(g)\} + \gamma \Delta S,$$

where $\gamma = 0.5$. Other values of $\gamma$ can also be selected. It is also possible to work with values which use the standard deviation rather than with the spread. In order not only to consider the value of a local maximum $\bar{S}_T(C_j)$, that is the value of $\bar{S}_T$ for an individual pitch $C_j$, but rather to use a representative value for a local maximum, all values exceeding half the spread $\sigma$ in a continuous interval $[g_a, g_b]$ can also be considered if that is $\bar{S}_T(g) > \sigma$ for $g_a \leq g \leq g_b$ and $\bar{S}_T(g) \leq \sigma$ for $g_a - \varepsilon < g < g_a$ and for $g_b \leq g \leq g_b + \varepsilon$ with a sufficiently small $\varepsilon$, e.g. due to the relative character of the pitch perception over wide ranges of the pitch:

$$\frac{g_b - g_a}{2} \xi,$$

where typically $u < \xi \leq 0.1$ is selected, i.e. $\bar{S}_T(g)$ may not exceed half the spread $\sigma$ in a range of $100 \cdot \xi\%$ about the interval $[g_a, g_b]$. Instead of a continuous interval $[g_a, g_b]$, it can also be advantageous in some applications to use an interval $[g_a, g_b]$ which contains subintervals ç which satisfy $g_a < g_\alpha < g_b$ and $g_a < g_\beta < g_b$ which are sufficiently small: $g_\alpha - g_\beta < \delta$, where $\delta < \mu \varepsilon$ with a sufficiently large $\mu : \mu > 1$. Everywhere in $[g_a, g_b]$ with the exception of the subintervals $[g_\alpha, g_\beta]$, $\bar{S}_T(g)$ exceeds half the spread $\sigma$. A weighted arithmetical mean $$\bar{C}_j = \frac{\sum_{k \in I_j} g_k \bar{S}_T(g_k)}{\sum_{k \in I_j} \bar{S}_T(g_k)},$$

where $I_j$ is the set of the indices of the jth interval $[g_a, g_b]$, can now e.g. be calculated for all the values of $\bar{S}_T(g)$ which lie within a continuous interval $[g_a, g_b]$ (or analogously for all values in an interval $[g_a, g_b]$ with subintervals $[g_\alpha, g_\beta]$) and which exceed half the spread $\sigma$. The index j in $[g_a, g_b]$ was omitted to avoid overloaded formulas. $I_j = \{a, \ldots, b\}$ therefore applies. In this manner, we obtain one or more (more precisely: L different) local maxima which are at the pitch(es) $\bar{C}_1, \ldots, \bar{C}_L$. It is now possible to continue in different manners:

(a) The CR therapeutic sounds are only adapted for the topmost central sound $\bar{C}_L$, where $\bar{C}_L > \bar{C}_j$ for all $j=1, \ldots, L-1$. As soon as the treatment has been carried out successfully in this pitch range, it is the turn of the next lower disposed central sound, that is $\bar{C}_{L-1}$.

(b) The CR therapeutic sounds are adapted in accordance with clinical criteria: It is e.g. possible to start with the central sound which belongs to the sound portion or the noise portion of tinnitus which is the loudest or which irritates the patient the most. After a successful treatment, the central sound follows which corresponds to the next loud or next irritating sound portion or noise portion.

(c) The first central sound upcoming for the treatment is selected by dynamic markers which are achieved within the framework of the examination carried out using the apparatus in accordance with the invention. The following dynamic markers can e.g. be used:

(I) A start is made with the central sound which belongs to the largest interval $[g_a, g_b]$ in which $\bar{S}_T(g)$ exceeds half the spread $\sigma$. Those regions of subintervals $[g_\alpha, g_\beta]$ should be deducted from the interval range $g_b - g_a$ in which $\bar{S}_T(g)$ does not exceed half the spread $\sigma$. After a successful therapy in the range of this central sound, it is the turn of the next central sound which belongs to the next broad pitch interval having a $\bar{S}_T(g)$ which is above the threshold (i.e. which exceeds half the spread $\sigma$).

(II) A start is made with the central tone which has the most pronounced entrainment overall (i.e. integrally or summed) in the associated above-threshold interval $[g_a, g_b]$. The associated integral power of the entrainment $\Lambda_j =$ is calculated for all central sounds $j=1, \ldots, L$ for this purpose: $\Lambda_j = \Sigma_{k \in I_j}(g_k)$. After a successful therapy, the central sound with the next strongest entrainment is treated.

(III) A start is made with the central sound which has the most pronounced relative entrainment (in relation to the extent of the above-threshold range) in the associated above-threshold interval $[g_a, g_b]$. The associated relative power of the entrainment $\gamma_j =$ is calculated for all central sounds $j=1, \ldots, L$ for this purpose:

$$\Upsilon_j = \bar{C}_j = \frac{\sum_{k \in I_j} \bar{S}_T(g_k)}{B_j},$$

where $B_j$ is the extent of the above-threshold range belonging to the jth central sound. $B_j = g_b - g_a$ applies in the simple case when $[g_a, g_b]$ does not contain any sub-threshold intervals $[g_\alpha, g_\beta]$. After a successful therapy, the central sound with the next strongest entrainment is treated.

(IV) The associated CR therapeutic sounds are determined for all central sounds and are used to treat all central sounds separately from one another in time and successively, wherein the treatment duration for the individual central sound can be adapted to clinical markers (i.e. to the loudness of the corresponding sound portion or noise portion in the tinnitus or in the irritation by the corresponding sound portion or noise portion) or to the above-defined dynamic markers ($B_j$, $\Lambda_j$ or $\gamma_j$), e.g. by a linear correlation: the louder the corresponding central sound, the longer it is treated. I.e. central sound 1 is treated with the associated CR therapeutic sounds during a specific time duration. Central sound 2 is then optionally treated during another time duration. The order in which the different central sounds are treated can be varied stochastically or deterministically (e.g. chaotically) or in a mixed stochastic/chaotic manner The order can, however, also always be influenced or predefined within a specific framework implemented e.g. by conditions in a random process by the clinical markers (loudness and/or irritation and/or by the dynamic markers ($B_j$, $\Lambda_j$ or $\gamma_j$).

(V) The associated CR therapeutic sounds are determined for all central sounds $\overline{C}_1, \ldots, \overline{C}_L$. In the further functional testing, only the CR therapeutic sounds for the CR therapy are used which actually satisfy the functional criteria (see below). In other words, if the different brain zones which belong to the different above-threshold intervals (and thus to the different central sounds $\overline{C}_1, \ldots, \overline{C}_L$) are connected to one another anatomically sufficiently and highly synaptically such that corresponding findings result in the functional testing (see below), all associated CR therapeutic sounds are used for the treatment. If two or more brain zones which belong to different central sounds prove to be not sufficiently synaptically connected to one another (see below), only one of the two central sounds is treated. The prioritization in the treatment of the respective central sounds takes place as described above.

Alternatively to the above-described method for the maximum determination, the maximum or maxima of $\overline{S}$ can also be determined by means of other test methods familiar to the skilled person (e.g. methods which are known under the term "change-point analyzer" in the literature and in the applications, see e.g. Taylor, Wayne (2000a), Change-Point Analyzer 2.0 shareware program, TaylorEnterprises, Libertyville, Ill. Web: http://www.variation.com/cpa).

The level of the n:m phase synchronization between the pulse train and the brain oscillation depends on the loudness of the sounds used for the stimulation. There are now a plurality of variants for this as to how the apparatus in accordance with the invention can operate.

1. Within the framework of a variant which is advantageous for practical performance since it can be carried out fast and simply, a loudness is preset and held constant during the entire examination (and in particular during the steps outlined in FIGS. 2ff). This is above all not a preferred procedure with tinnitus patients. Such a fast procedure can be considered for patients who do not suffer from tinnitus (typically accompanied by hearing impairments), but rather e.g. from depression, who are not stimulated in the speech range (and not in the high-frequency range in which hearing impairments are more frequently found) and in whom pathological findings (that is a hearing impairment) could be excluded in a previous threshold audiometry. The preset loudness should be selected either close to the threshold or up to 20 dB above the auditory threshold, optionally even greater (if the entrainment should be difficult to carry out).

2. The loudness of the sounds used for the stimulation is determined by interpolation and extrapolation from a classical threshold audiogram. This variant can also be carried out fast and therefore very practically. With a classical threshold audiogram, the auditory threshold is determined at comparatively few sampling points. This procedure has error potential with respect to the interpolation since there are in principle small hearing dips which are, however, not arbitrarily frequent. The extent of these hearing impairments can be so tightly circumscribed in the frequency space that these small hearing dips cannot be detected due to the few sampling points of the threshold audiogram. The loudness of the stimuli at frequencies in the range of such a hearing dip would have to be raised to compensate the hearing impairment. It can occur in this manner that a stimulation is used which is much too low (in comparison with the auditory threshold), particularly in the range of a hearing dip which is also frequently the frequency range of the tinnitus e.g. with tinnitus patients so that no entrainment (FIG. 2) can be observed. This variant has the difficulty with respect to the extrapolation that a high-frequency amblyacousia is present above the highest sampling point of the threshold audiogram. The stimulation sounds would then also not be loud enough in this (extrapolated) range in this case and a misleading result would be produced.

3. To scan (measure) the auditory threshold in sufficient detail or density, the following variant can in particular be used with patients who have a hearing reduction or hearing impairment (e.g. in accordance with standard threshold audiometry) or with patients who were not able to achieve sufficiently good results with the two aforesaid variants or in whom a suspected narrow-band hearing dip is present for another medical reason:

A Békésy audiometry (Békésy G. v.: A new audiometer. Acta oto-laryngol. (Stockh.) 35 (1947) 411; Lehnhardt E., Laszig R.: Praxis der Audiometrie. Thieme, Stuttgart, 9th Edition, 2009) is carried out before the measurement illustrated in FIG. 2 to continuously scan the auditory threshold over the frequency axis. For this purpose, the frequency is continuously varied in a stepless manner from e.g. 100 Hz to 10,000 Hz in the auditory measurement. With tinnitus patients having high-frequency tinnitus (e.g. >8000 Hz) or with a high frequency hearing impairment, the frequency is varied even further upwardly (e.g. up to 130,000 Hz or 16,000 Hz) within e.g. 400 seconds or 200 seconds. The intensity is regulated up to 120 dB in small steps of 0.25 dB and at a speed of e.g. 2.5 dB/sec or 5 dB/sec. The sound is administered either as a continuous tone or as a pulse tone (of 200 ms or 150 ms duration). The preferred variant is the pulse tone method since it determines the auditory threshold for pulse tones and pulse tones are used for the further examination of the entrainment. Ratios such as 1:1 or 1:3 can be selected as the pulse break ratio (that is the ratio between the duration of the individual pulse tone and the following break). In the pulse variant, the stimulation frequency (repetition rate at which the pulse tone is administered) can also be adapted to the dominant spectral frequency peak of the pathological oscillation measured via the sensors (e.g. EEG electrodes) in a small, whole-number n:m ratio (where n and m are small whole numbers).

The patient regulates the loudness reducer via a hand switch (dB regulator). The loudness of the sound reduces as long as the hand switch is pressed. If the hand switch is not pressed, the loudness increases again. The intensity (loudness) is in this respect (as mentioned above) regulated at a speed of e.g. 2.5 dB/sec or 5 dB/sec in 0.25 dB steps. Other step values, e.g. 2 dB, can also be selected. Less preferably, a completely stepless regulation of the intensity can be selected. A curve is hereby obtained which extends in jagged form since the auditory threshold regulated by the patient moves to and fro between a just already audible and a no longer audible intensity level.

If the Békésy audiometry is carried out separately before the entrainment examination outlined in FIG. 2, a continuous auditory threshold dependent on the frequency (i.e. on the pitch T) is determined in that the local extremes which belong to the just already audible intensity levels are interpolated (and optionally extrapolated after high values). The intensity levels of this auditory threshold are called a continuous auditory threshold and are selected as intensity values for the periodic pulse train of FIG. 2. Alternatively, a constant intensity level of e.g. 2 dB or 3 dB or 5 dB or of larger values such as 10 dB or even 20 dB or more can be added to the auditory threshold independently of the respective frequency (i.e. pitch T). This curve is called the continuous intensity threshold. The values of the continuous intensity threshold are used as intensity values for the periodic pulse train of FIG. 2. Such increased intensity values can be advantageous when no sufficiently strong entrainment can be caused using the intensity values corresponding to the auditory threshold.

An isophone can also be determined instead of the continuous intensity threshold. Since this, however, typically only takes place at a limited number frequencies so that an interpolation and (at the upper limit) an extrapolation is necessary, their value is typically limited if they are not prepared in a time-consuming and detailed manner. A continuous intensity threshold is typically absolutely sufficient for the purposes of the apparatus in accordance with the invention.

If the Békésy audiometry is carried out simultaneously with the entrainment examination outlined in FIG. 2, a longer examination duration than with only the Békésy audiometry can be selected (depending on the stimulation frequency $F_{stim}$). This is necessary to obtain a sufficient number of stimulation periods $T_{stim}$ for the calculation of the phase synchronization index for the respective pitch interval (in which an entrainment should be detected). The targeted precision of the frequency resolution (i.e. pitch resolution) is above all determined by the following parameter:

Number of stimulation periods $N_{stim}$ per window width $\Delta F$ (difference of the upper and lower pitches in Hz of the window). This parameter determines the examination period $T_{ges}$.

The stimulation frequency (repetition rate) $F_{stim}$ and thus the stimulation period $T_{sum}$ are based on the dominant frequency $\hat{F}$ (i.e. on the frequency peak in the spectrum) of the pathological neural collective (synchronized) oscillation which is to be desynchronized. In the most favorable case, the stimulation frequency $F_{stim}$ is selected such that it is as similar as possible to the dominant frequency, i.e. $F_{stim} \approx \hat{F}$, where $F_{stim}$ should not differ from $\hat{F}$ by substantially more than 5% or 10% or 20%. The method is robust since a deviation of the two frequencies by an increase in the loudness of the stimuli can be compensated to a degree sufficient for practical use. Work should, however, be carried out with a loudness which is as low as possible since only then is the spatial stimulation influence in the brain spatially very selective and some patients perceive stimuli which are too loud as unpleasant and tiring.

In a less preferred embodiment of the apparatus in accordance with the invention, $F_{stim}$ is not adapted to $\hat{F}$, but a frequency is rather a priori selected for the frequency bands familiar to the skilled person. If the deviation of the stimulation frequency $F_{stim}$ from the dominant frequency $\hat{F}$ is so large that the results of the entrainment are not pronounced enough, this can be compensated by an increase in the loudness. A fixed amount of e.g. 5 dB is added e.g. to the auditory threshold (which is determined as described below) for this purpose. The pitch is steplessly continuously and linearly varied (i.e. at a constant speed) from $F_{botom}$ to $F_{top}$ e.g. from $F_{bottom}$=100 Hz to $F_{top}$=13,000 Hz. The pitch can also increase non-linearly, e.g. logarithmically (in another embodiment). In the case of a linear increase of the pitch, the examination time $T_{ges}$ is calculated as follows:

$$T_{ges} = \frac{F_{top} - F_{bottom}}{\Delta F} N_{stim} T_{stim},$$

where $N_{stim} T_{stim}$ is the time for running through the window width $\Delta F$ with $N_{stim}$ stimulation periods of a duration $T_{stim}$. Example: With the parameters $N_{stim}$=100, $\Delta F$=500 Hz, $F_{bottom}$=100 Hz, $F_{top}$=13,000 Hz, a stimulation frequency $F_{stim}$=1.5 Hz and thus a stimulation period $T_{stim}$=0.666 s results in the event of a dominant frequency $\hat{F}$=1.5 Hz. An examination time $$T_{ges} = \frac{F_{top} - F_{bottom}}{\Delta F} N_{stim} T_{stim} = \frac{F_{top} - F_{bottom}}{F_{stim} \Delta F} N_{stim} = 28.7 \text{ min.}$$

thus results. If, in contrast, the window width $\Delta F$=500 Hz should only be scanned with $N_{stim}$=50 stimulation periods, a less good definition is obtained between the frequency ranges with and without entrainment, but the examination time is halved: $T_{ges}$=14.3 min.

The dominant frequency $\hat{F}$=1.5 Hz is in the lower range of the so-called delta frequency band (1-4 Hz). If the dominant frequency is larger, a much shorter examination time results. For $\hat{F}$=3 Hz=$F_{stim}$ (and otherwise the same parameters) e.g. the examination time $T_{ges}$=14.3 min is obtained for A $N_{stim}$=100 and $T_{ges}$=7.2 min for $N_{stim}$=50. If the dominant frequency is in the theta frequency band (5-8 Hz) and if e.g. $\hat{F}$=6 Hz, we obtain with $F_{stim}$=$\hat{F}$ the associated examination time $T_{ges}$=7.2 min for $N_{stim}$=100 and $T_{ges}$=3.6 min for $N_{stim}$=50.

The stimulation frequency very decisively determines the examination time. To keep the examination time $T_{ges}$ as small as possible, the number of stimulation periods per window width $N_{stim}/\Delta F$ can, on the one hand, be selected as small. On the other hand or in addition, the stimulation frequency $F_{stim}$ can also be selected as larger than the dominant frequency $\hat{F}$. This in particular produces a shortening of the examination time $T_{ges}$ when the dominant frequency $\hat{F}$ is in the delta frequency band (1-4 Hz) and not in the theta frequency band (5-8 Hz). If the dominant frequency $\hat{F}$ is measured, the stimulation frequency $F_{stim}$ can be selected such that it is in a small whole number relationship with $$\hat{F}: \frac{F_{stim}}{\hat{F}} = \frac{n}{m} > 1,$$

where n and m are small whole numbers. As the examination time reduces, however, the quality of the scanning of the auditory threshold can decrease. This is, however, not really a serious point since the results are sufficiently stable with respect to a variation of the loudness of the stimulation sounds.

In summary, the following variants result for the method realized by the apparatus in accordance with the invention for determining the n:m phase synchronization between the pulse train and the brain oscillation:

- the loudness of the stimuli is preset (less preferred)
- the loudness is adapted to a conventional audiodiagram (that is determined at few sampling points); for this purpose, the continuous extent of the auditory threshold can be approximated by interpolation and extrapolation.
- A Békéshy audiogram delivers the quasi-continuous auditory threshold. If the Békéshy audiogram is not carried out in parallel with the entertainment examination, a continuous auditory threshold can be prepared by interpolation (and optionally also by extrapolation at the upper limit) of the local extremes of the (jagged) Békéshy audiodiagram which are perceived as just audible. The Békéshy audiogram can, however, also be carried out in an elegant manner in parallel with the entrainment examination. The examination time can be relevantly shortened in this manner.
- If the intensity values (loudness values) of the auditory threshold (determined by a classical audiogram or by a Békéshy audiometry) do not allow a sufficiently strong entrainment (that is an n:m phase synchronization between the pulse train and the brain oscillation which is not sufficiently strong), a strong stimulus intensity can be selected either (preferably) by using a continuous intensity threshold or an isophone (see above). Depending on the result, the deviation of the continuous intensity threshold or of the isophone from the auditory threshold can be increased until finally a sufficiently strong entrainment is reached.

This procedure donates a central sound C, that is a central frequency (in the sense of a pitch) C, which can be considered as the anatomic center of a synchronous focus in the central auditory system (e.g. in the auditory cortex).

I.1.b Detection of Intervals Using Amplitude Minima

Figure 3A:
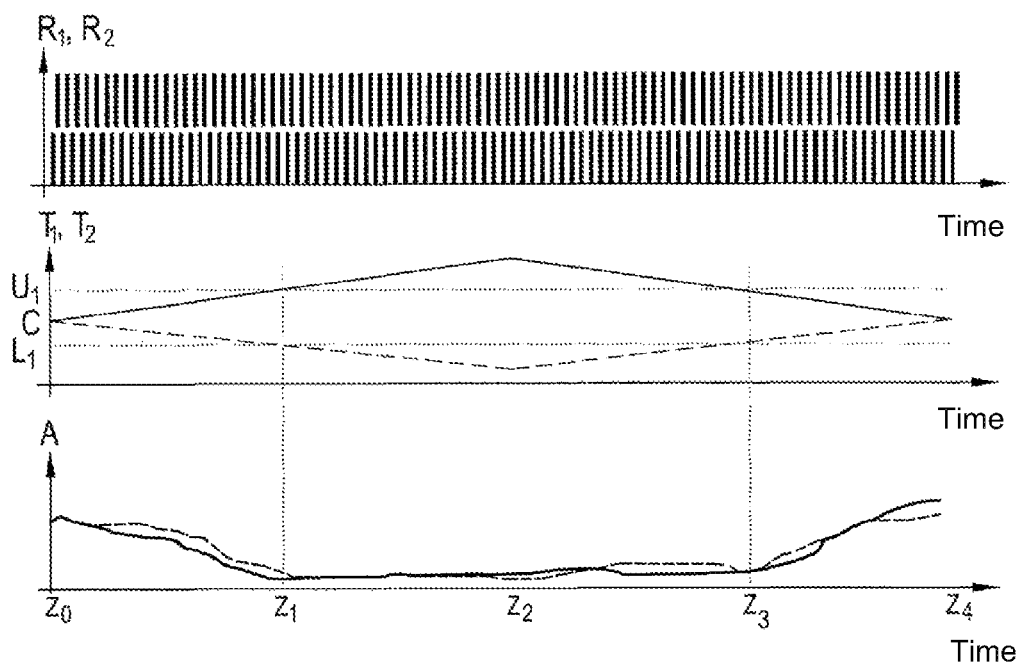
FIG. 3a illustrates a chart showing the application of two constant periodic out-of-phase pulse trains, wherein the pitches of both pulse trains are varied continuously and oppositely.
Figure 3B:
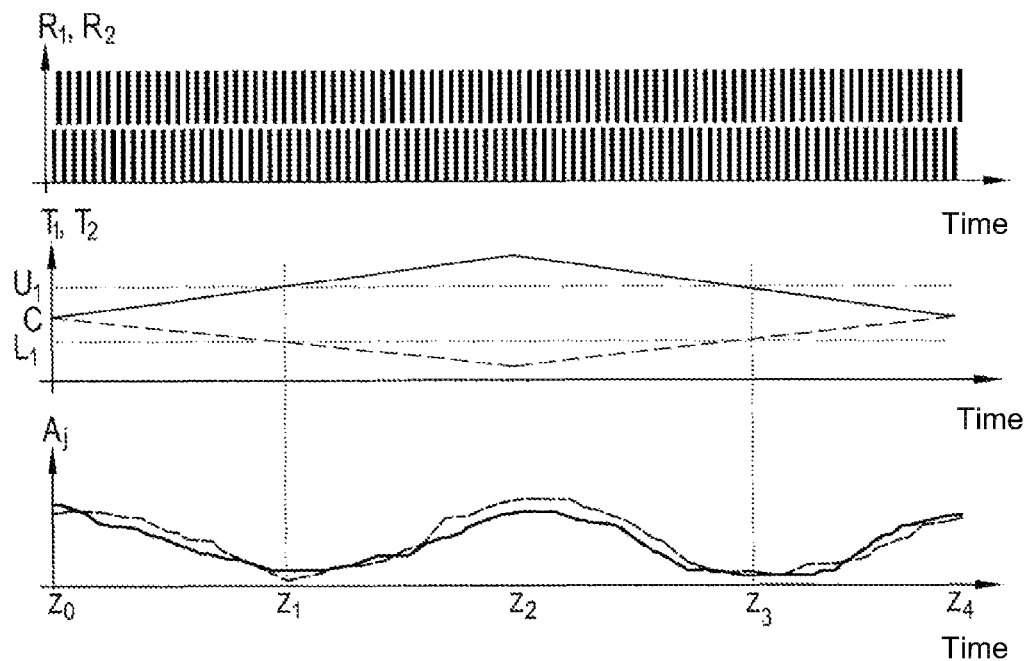
FIG. 3b illustrates a chart showing the application of two constant periodic out-of-phase pulse trains, wherein the pitches of both pulse trains are varied continuously and oppositely.

The goal of this step is to determine the ideal distance between adjacent therapeutic sounds. For this purpose, two constant (in time) periodic, phase-shifted, in particular out-of-phase pulse trains are applied, wherein the pitch of both pulse trains are varied continuously and oppositely (FIG. 3). If the pitches of both pulse trains are close to one another, the same region in the auditory cortex (or the same regions in different downstream regions of the central auditory pathway) in the brain is/are substantially stimulated by both pulse trains (i.e. with a large spatial overlap). This overlap is due to the fact that—as described by the so-called tuning curves—adjacent neurons are admittedly ideally excited by sound of different frequencies, but also by sound of adjacent frequencies, albeit typically less strong. In this case, a periodic stimulation with double the stimulation frequency $F_{stim}$ is substantially carried out. If the pitches of both pulse trains are too far apart, so that the two excited brain areas no longer interact sufficiently strongly (are anatomically coupled) as a result of the strength of the anatomic networking reducing with the distance, two different sites in the brain are excited in a phase-shifted (out-of-phase) manner. If the electrical field generated by both excited neural populations should have exactly the same amplitude, the fields of both neural populations can at least partly cancel each other out—depending on the anatomical location of the neurons arranged in a dipolar manner. In this case, in a first approximation the total electrical field disappears in the band pass frequency range of the simple and doubled stimulation frequency $F_{stim}$. If the excitation of the two neural populations should not result in an equally strong field (e.g. as a result of different sizes of the neural populations and/or of a different anatomical alignment of the respective participating neurons, etc.), a field results which is different from zero in total, which results in values correspondingly differing from zero in the band pass range of the simple and doubled stimulation frequency $F_{stim}$ (FIG. 3b). The smallest values of the amplitude—and thus of the band pass ranges corresponding to the simple and doubled stimulation frequency $F_{stim}$—of the electrical field generated by both neural populations result when the two neural populations interact anatomically (that is not localized too far away from one another) and are desynchronized by the out-of-phase stimulation, that is Cr stimulation (FIGS. 3a, 3b).

Analogously to the above problem (FIG. 2) in which maxima were detected, a minimum detection FIG. 3b) or a detection of the margins of an extended range of small values (FIG. 3a) now results here (using the same methods). This can be carried out using data analysis methods which are familiar to the skilled person. The averaging technique used for the maximum detection (FIG. 2) can e.g. be used and an inflection point can now be detected instead of a maximum (as in FIG. 2).

FIG. 3a shows the application of two constant periodic out-of-phase pulse trains, wherein the pitches of both pulse trains are varied continuously and oppositely. The x axis is the time axis in all three illustrations. The topmost illustration schematically shows the extent of both acoustic stimulus sequences. A single black bar stands for a pure sound of a pitch T which is folded using a Hamming window or (less preferably) with a cosine function or another, preferably smooth envelope which typically restricts the time extent of the sound. The middle illustration schematically shows how the pitches $T_1$ and $T_2$ of the two periodic stimulus sequences are continuously varied. The lower illustration schematically shows the extent of the amplitude (e.g. Hilbert amplitude or integral of the power in the examined frequency band pass) which belongs to the stimulation frequency $F_{stim}$ ($A_1$) or double the stimulation frequency ($A_2$).

FIG. 3b shows the application of two constant periodic out-of-phase pulse trains, wherein the pitches of both pulse trains are varied continuously and oppositely. Format as in FIG. 3a.

A therapeutic sound $U_1$ disposed above the central sound C and a therapeutic sound $L_1$ disposed below the central sound C are obtained by this procedure.

Further possible therapeutic sounds above the central sound C ($U_2$, $U_3$, . . . ) or below the central sound C ($L_2$, $L_3$, . . . ) are now determined iteratively in that two out-of-phase pulse sequences are administered, wherein the pitch of the one pulse sequence is constant at the respective output therapeutic sound (e.g. $U_1$ in FIG. 4) and the pitch of the other pulse sequence first increases and then falls again for the detection of the next higher therapeutic sound (FIG. 4). Analogously to FIG. 3a or FIG. 3b, the minima (FIG. 4) of the amplitude of the band pass is detected (as described above), said band pass corresponding to the simple or doubled stimulation frequency $F_{stim}$. This is carried out iteratively for so long as relevant minima (FIG. 5) or inflection points can be detected. Different criteria for the relevance can be used in this respect. E.g. only minima are accepted which differ sufficiently strongly from the mean value and from the standard deviation. A plurality of methods of data analysis and statistical test methods are available to the skilled person here.

Analogously to the respectively next higher therapeutic sounds $U_2$, $U_3$, . . . , the respective next lower therapeutic sounds $L_2$ (FIG. 6), $L_3$ (FIG. 7) . . . are also detected.

FIG. 4 shows the application of two constant periodic out-of-phase pulse trains, wherein the pitch ($U_2$) of only one of the two pulse trains is continuously varied in a rising and then falling manner. The pitch ($U_1$) of the other pulse train remains constant. Format as in FIG. 3a.

FIG. 5 shows the application of two constant periodic out-of-phase pulse trains, wherein the pitch ($U_3$) of only one of the two pulse trains is continuously varied in a rising and then falling manner. The pitch ($U_2$) of the other pulse train remains constant. Format as in FIG. 3a.

FIG. 6 shows the application of two constant periodic out-of-phase pulse trains, wherein the pitch ($L_2$) of only one of the two pulse trains is continuously varied in a falling and then rising manner. The pitch ($L_1$) of the other pulse train remains constant. Format as in FIG. 3a.

FIG. 7 shows the application of two constant periodic out-of-phase pulse trains, wherein the pitch ($L_3$) of only one of the two pulse trains is continuously varied in a falling and then rising manner. The pitch ($L_2$) of the other pulse train remains constant. Format as in FIG. 3a.

Subvariant I.2: Determining the CR Therapeutic Sounds without Central Sound

This is a less preferred variant since with small regions which are characterized by strong entrainment (and which correspond to a small focus or to small focal points of the pathological synchronization in the central nervous system), no further therapeutic sound can be positioned in the region with strong entrainment next to the central sound in an unfavorable case. In contrast to this, two symmetrically arranged therapeutic sounds can typically be positioned in such a case without a central sound.

Figure 8:
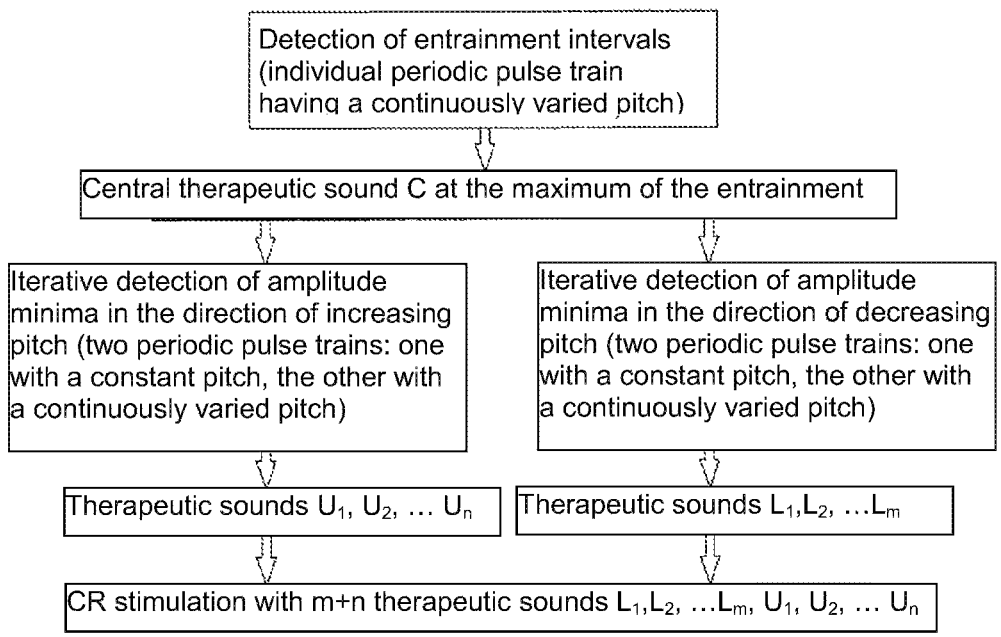
FIG. 8 illustrates a flowchart of the routine of the method in accordance with the invention in the variant with a centrally arranged therapeutic sound (C, so-called central sound).

FIG. 8 shows a flowchart of the routine of the method in accordance with the invention in the variant with a centrally arranged therapeutic sound (C, so-called central sound).

After determining the central sound C, it is selected as the therapeutic sound. The next higher therapeutic sound $U_1$ or the next lower therapeutic sound $L_1$ are detected—analogously to the determination of $U_2$ or $L_2$ in the case of the variant without a central sound (see above)—in that the pitch of only one stimulus sequence increases in the two out-of-phase stimulus sequences (for the determination of $U_1$, FIG. 10) or falls (for the determination of $L_1$), whereas the respective pitch of the other stimulus sequence remains constantly set to C. The determination of the respective minima or inflection points of the amplitude takes place as described above (for subvariant I.1). The further iterative determination of the further next higher therapeutic sounds $U_2$, $U_3$, . . . or the next lower therapeutic sounds $L_2$, $L_3$, . . . equally takes place as described above (for subvariant I.1).

Figure 9:
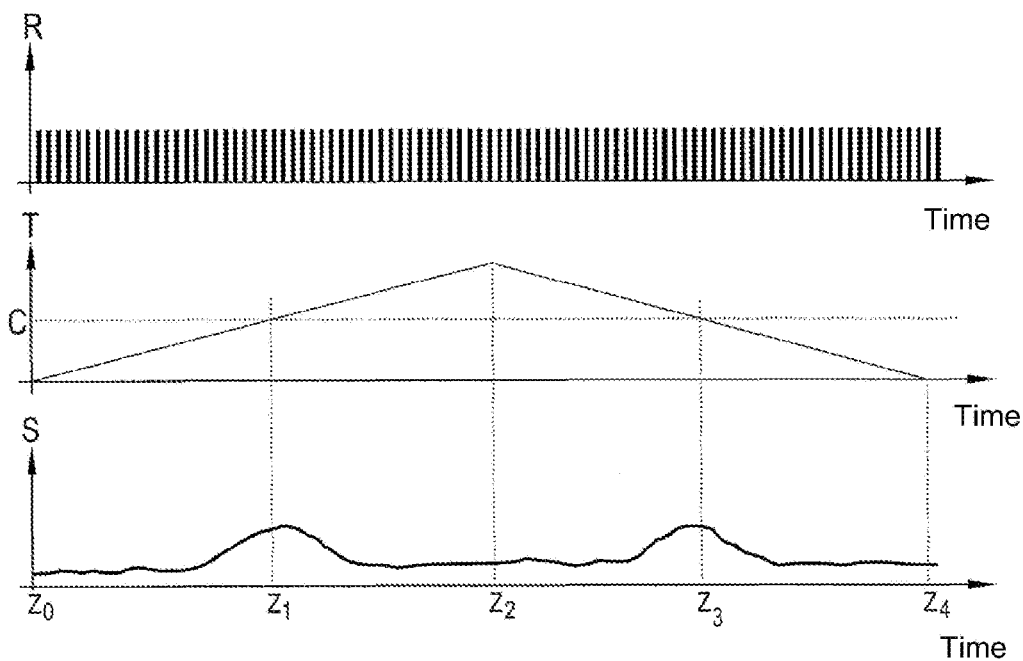
FIG. 9 illustrates a chart showing the detection of entrainment intervals (individual periodic pulse train with a continuously varied pitch). This step is identical in the methods in accordance with the invention with and without a central sound.

FIG. 9 shows the detection of entrainment intervals (individual periodic pulse train with a continuously varied pitch). This step is identical in the methods in accordance with the invention with and without a central sound; FIG. 9 and FIG. 2 are accordingly identical.

Figure 10:
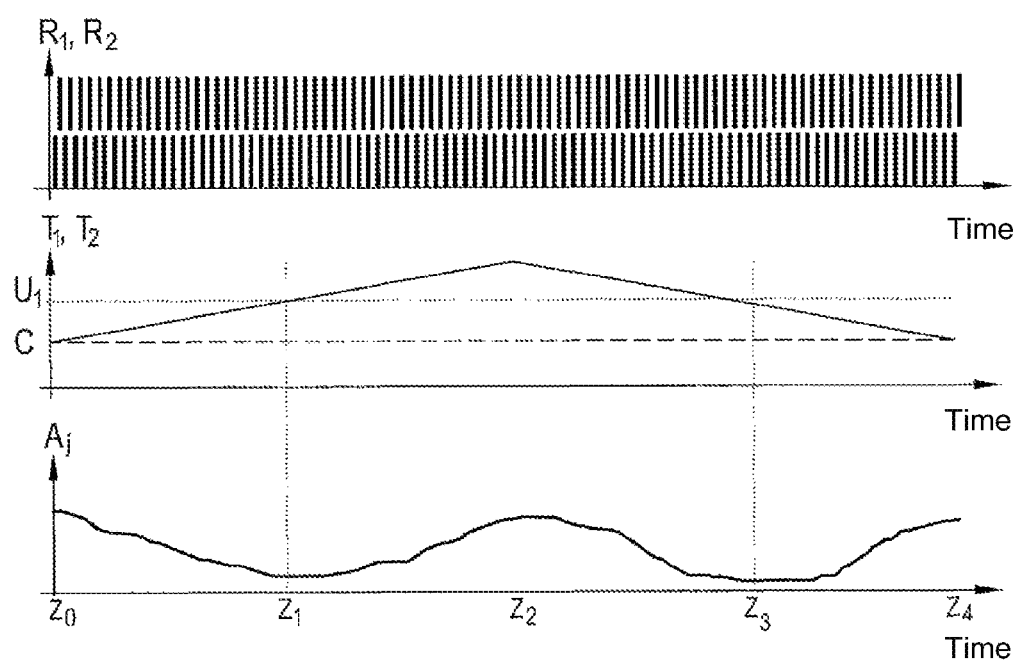
FIG. 10 illustrates a chart showing the application of two constant periodic out-of-phase pulse trains ($R_1$ and $R_2$) which comprise pure sounds with the respective pitches $T_1$ and $T_2$.

FIG. 10 shows the application of two constant periodic out-of-phase pulse trains ($R_1$ and $R_2$) which comprise pure sounds with the respective pitches $T_1$ and $T_2$. The pitch (solid line) of only one of the two pulse trains is continuously varied in a rising and then falling manner. The pith (C, dashed line) of the other pulse train remains constant. Format as in FIG. 3a.

Minimal Variants:

There are embodiment variants of the apparatus in accordance with the invention and of the method in accordance with the invention in which the two steps (shown schematically in FIG. 1), the detection of entrainment intervals (by means of an individual periodic pulse train) and the detection of intervals with amplitude minima (by means of two periodic pulse trains) are not carried out, but rather only one of the two steps.

Minimal Variant 1:

Only a detection of entrainment intervals is carried out (by means of a single periodic pulse train). 4 therapeutic sounds are e.g. adapted to the maximum hereby determined in a predefined frequency ratio. Example: If the maximum is at the pitch C (see FIG. 1), logarithmically equidistant therapeutic sounds can e.g. be selected in an interval of e.g. 77% to 140% of C. It is advantageous in this respect that this variant is considerably faster than the variant with an additional subsequent detection of intervals with amplitude minima (by means of two periodic pulse trains).

Minimal Variant 2:

Only an estimate of the suitable distance of the therapeutic sounds is carried out. The start frequency required for this is selected in advance in accordance with disease-specific criteria (see below). Only a detection of intervals with amplitude minima is carried out (by means of two periodic pulse trains). This is advantageous with diseases in which no synchronous focus is to be expected in the auditory cortex (or in the central auditory system) in a region associated with a hearing impairment, that is e.g. with ADHS, depression, schizophrenia, etc. A start frequency is e.g. fixed in the speech range which can e.g. be advantageous with schizophrenics with acoustic hallucinations since they have pathological activity in the associated auditory cortex. This start frequency corresponds to the pitch C (see FIG. 1). Starting from the C fixed in this manner, suitably distant therapeutic sounds are determined by means of detection of intervals with amplitude minima (by means of two periodic pulse trains). Minimal variant 2 is faster than the variant with a prior detection of entrainment intervals (by means of a single periodic pulse train).

Occurrence of More than One Synchronous Focus

If more than one maximum results in the part interval [$z_0, z_2$] on the detection of the maxima (FIG. 2), the algorithm described here is started for each local maximum until all maxima have been worked through and thus all relevant pitch part intervals are covered.

(II) Discrete (or Coarse-Step) Variation of One (or More) Stimulus Property/Properties During the Application of a Strictly Periodic Pulse Train:

Instead of the above-described continuous variation of one or more stimulus properties, the above-listed entertainment analyses (with a periodically applied stimulation) or amplitude analyses (with two out-of-phase periodic stimuli) can e.g. also only be carried out for a discrete set of values of this stimulus property or these stimulus properties. Such a coarse-step procedure can be disadvantageous since optionally circumscribed hearing dips and associated circumscribed synchronous focal points cannot be detected. The step size can be selected as sufficiently small to avoid this. In this case, however, the continuous variation of the stimulus property or properties is typically the faster method. This is due to the fact that with the discrete variation for a specific value of a stimulus property a sufficiently large number, e.g. N, identical individual stimuli have to be applied in the periodic stimulus sequence to be able to carry out an analysis (see above). In the variant with a continuous variation, these N different stimuli are evaluated in an analysis interval which is time shifted over the data set for an internal of values of the stimulus property. I.e. in the latter case, the resolution with respect to the stimulus property or properties, e.g. with respect to the pitch of the stimuli (see above), is blurred. This blurring is, however, advantageous since it brings about a substantial time saving and the therapeutic stimulation method does not require any greater accuracy in the detection of the synchronous focal points, on the one hand, and in the estimation of suitable distances between the stimulus properties (e.g. pitches) between the therapeutic sounds.

The invention claimed is:

1. A method of stimulating neurons having a pathologically synchronous and oscillatory neural activity, the method comprising:
   applying pulsed sounds to a patient, wherein the sounds stimulate neurons of the patient;
   recording measured signals that reproduce a neural activity of the stimulated neurons;
   applying a first pulse train having a varied pitch;
   selecting at least one first pitch range or at least one first pitch in or at which a phase synchronization is present between the first pulse train and the neural activity with reference to the measured signals recorded in response to the application of the first pulse train;
   applying two phase-shifted second pulse trains, wherein respective pitches of the two second pulse trains are varied relative to each other and a start value is selected for the pitch of the second pulse trains in dependence on the at least one first pitch range or on the at least one first pitch; and
   selecting at least one second pitch range or at least one second pitch in or at which an amplitude of the neural activity is minimal with reference to the measured signals recorded in response to the application of the second pulse trains.

2. The method in accordance with claim 1, further comprising varying oppositely the respective pitches of the two second pulse trains.

3. The method in accordance with claim 1, wherein the phase-shift of the two second pulse trains amounts train mounts to 180°.

4. The method in accordance with claim 1, further comprising selecting a pitch at which the phase synchronization between the first pulse train and the neural activity is a maximum with reference to the measured signals recorded in response to the application of the first pulse train.

5. The method in accordance with claim 4, further comprising using the selected at least one first pitch as a start value for the pitch of the second pulse trains.

6. The method in accordance with claim 1, further comprising selecting one of the at least one first pitch range and the at least one first pitch in or at which an n:m phase difference $\Psi_{n,m}(t)=m\varphi_1(t)-m\varphi_2(t)$ is a maximum with reference to the measured signals recorded in response to the application of the first pulse train, wherein $\varphi_1(t)$ is the phase of the first pulse train, $\varphi_2(t)$ is the phase of neural activity and n and m are whole numbers.

7. The method in accordance with claim 1, further comprising:
   applying two phase-shifted third pulse trains, wherein the pitch of one of the third pulse trains is varied and the pitch of the other third pulse train is constant; and
   selecting a start value for the pitch of the two third pulse trains in dependence on the selected at least one second pitch range or on the selected at least one second pitch, wherein the start value for the pitch of the third pulse trains is above the start value for the pitch of the second pulse trains, and
   wherein at least one third pitch range or at least one third pitch in or at which the amplitude of the neural activity is minimal with reference to the measured signals recorded in response to the application of the third pulse trains is selected.

8. The method in accordance with claim 7, further comprising iteratively repeating the application of the two phase-shifted third pulse trains.

9. The method in accordance with claim 7, further comprising:
   applying two phase-shifted fourth pulse trains, wherein the pitch of one of the fourth pulse trains is varied and the pitch of the other fourth pulse train is constant;
   selecting a start value for the pitch of the two fourth pulse trains in dependence on the selected at least one second pitch range or on the selected at least one second pitch, wherein the start value for the pitch of the fourth pulse trains is below the start value for the pitch of the second pulse trains, and
   wherein at least one fourth pitch range or at least one fourth pitch in or at which the amplitude of the neural activity is minimal with reference to the measured signals recorded in response to the application of the fourth pulse trains is selected.

10. The method in accordance with claim 9, further comprising iteratively repeating the application of the two phase-shifted fourth pulse trains.

11. The method in accordance with claim 9, further comprising applying two phase-shifted third pulse trains and selecting sounds having the at least one second pitch, having the at least one third pitch and having the at least one fourth pitch for a therapeutic stimulation of the patient.

12. The method in accordance with claim 11, further comprising additionally selecting a sound having the at least one first pitch for the therapeutic stimulation of the patient.

13. The method in accordance with claim 11, wherein the therapeutic stimulation is a coordinated reset stimulation.

14. The method in accordance with claim 1, further comprising:
   varying the pitch of a first pulse train of the two second pulse trains; and
   maintaining the pitch of a second pulse train of the two second pulse trains as constant.

15. A method of stimulating neurons having a pathologically synchronous and oscillatory neural activity, the method comprising:
   applying pulsed sounds to a patient, wherein the sounds stimulate neurons of the patient;
   recording measured signals that reproduce a neural activity of the stimulated neurons;

applying a first pulse train having a varied frequency;
selecting at least one first frequency range or at least one first frequency in or at which a phase synchronization is present between the first pulse train and the neural activity with reference to the measured signals recorded in response to the application of the first pulse train;
applying two phase-shifted second pulse trains, wherein respective frequencies of the two phase-shifted second pulse trains are varied relative to each other and a start value is selected for the frequency of the second pulse trains in dependence on the at least one first frequency range or on the at least one first frequency; and
selecting at least one second frequency range or at least one second frequency in or at which an amplitude of the neural activity is minimal with reference to the measured signals recorded in response to the application of the second pulse trains.

16. The method in accordance with claim 15, further comprising varying oppositely the respective frequencies of the two second pulse trains.

17. The method in accordance with claim 15, wherein the frequency of a first pulse train of the two second pulse trains is varied and the frequency of a second pulse train of the two second pulse trains is maintained as constant.

* * * * *